United States Patent
Sughrue et al.

(10) Patent No.: US 11,461,917 B1
(45) Date of Patent: Oct. 4, 2022

(54) MEASURING 3-DIMENSIONAL DISTANCES IN MEDICAL IMAGING DATA

(71) Applicant: Omniscient Neurotechnology Pty Limited, Sydney (AU)

(72) Inventors: Michael Edward Sughrue, Sydney (AU); Stephane Philippe Doyen, Glebe (AU); Kieran Mann, San Diego, CA (US)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/407,879

(22) Filed: Aug. 20, 2021

(51) Int. Cl.
*G06K 9/00* (2022.01)
*G06T 7/62* (2017.01)
*G06T 3/00* (2006.01)
*G06T 7/00* (2017.01)
*G16H 30/40* (2018.01)

(52) U.S. Cl.
CPC .............. *G06T 7/62* (2017.01); *G06T 3/0006* (2013.01); *G06T 7/0012* (2013.01); *G16H 30/40* (2018.01); *G06T 2207/10088* (2013.01); *G06T 2207/30016* (2013.01); *G06T 2207/30096* (2013.01)

(58) Field of Classification Search
None
See application file for complete search history.

(56) References Cited

U.S. PATENT DOCUMENTS

2003/0053697 A1* 3/2003 Aylward .................. G06T 7/64
382/203
2018/0315191 A1* 11/2018 Meng ....................... G06T 7/11

OTHER PUBLICATIONS

Tran: "Close Weighted Shortest Paths on 3D Terrain Surfaces" SIGSPATIAL '20, Nov. 3-6, 2020, pp. 1-11. (Year: 2020).*

* cited by examiner

*Primary Examiner* — Wei Wen Yang
(74) *Attorney, Agent, or Firm* — Fish & Richardson P.C.

(57) ABSTRACT

Methods and systems for measuring 3-dimensional distances on medical images are described. One example method includes receiving at least a first 2-dimensional image on a first plane and a second 2-dimensional image on a second plane, wherein the first plane and the second plane are different planes, selecting a first point on the first 2-dimensional image as a start point, selecting a second point on the second 2-dimensional image as an end point, determining a shortest path between the start point and the end point, performing a measurement of the shortest path between the start point and the end point, and, taking an action based on the measurement.

19 Claims, 5 Drawing Sheets

MEASURING 3-DIMENSIONAL DISTANCES IN MEDICAL IMAGING DATA

TECHNICAL FIELD

The present disclosure generally relates to measuring distances in medical images.

BACKGROUND

Planning for surgery and other medical procedures regularly involves in depth scrutiny of medical images including the ability to measure objects, e.g., a tumor, on screen to get an accurate size measurement. However, surgery planning systems typically only allow measurements on 2D planes which represent a challenge as often the objects to be measured are three dimensional and require additional knowledge, for example, of the thickness of images in order to calculate the size of an object. This can lead to inaccurate measurements which can be problematic for calculating, e.g., a dose of radiation, or the insertion trajectory of a needle.

SUMMARY

It is desirable in medical imaging systems to be able to make measurements across canonical planes, i.e., in 3-dimensions. Such measurements enable more accurate measurement (e.g., in terms of a dimension or volume) of objects reflected in medical images, allowing for more accurate dosing (e.g., drug and/or radiation dosing) and/or guidance for surgical procedures. For example, while estimates of z-dimensional measurements of anatomical features from traditional methods may be accurate to only a few millimeters. The methods described herein are accurate to within 1 mm In one aspect, a method of measuring 3-dimensional distances on medical images can include, receiving at least a first 2-dimensional image on a first plane and a second 2-dimensional image on a second plane, wherein the first plane and the second plane are different planes, selecting a first point on the first 2-dimensional image as a start point, selecting a second point on the second 2-dimensional image as an end point, determining a shortest path between the start point and the end point, performing a measurement of the shortest path between the start point and the end point, and, taking an action based on the measurement.

In some implementations determining a shortest path between the start point and the end point includes performing raycasting to determine a projection of the co-ordinates of the first selected point on the first 2-dimensional image and the second selected point on the second selected image from 2-dimensional space to three dimensional space.

In some implementations taking an action includes converting the projected co-ordinates from system units to real world units including performing an affine transformation; and measuring the distance between the first selected point and the second selected point using a geometric function.

In some implementations the first plane and the second plane are each selected from axial, sagittal, coronal, and oblique planes.

In some implementations the first image is selected from a sequence of 2-dimensional medical images on the first plane, the sequence of images being images of a human organ, and the start point is a first point of interest; and, the second image is selected from a sequence of 2-dimensional medical images on the second plane, the sequence of images being images of a human organ, and the start point is a first point of interest.

In some implementations the first image and the second image are orthogonal to each other.

In some implementations the method further includes measuring a length and a width of a feature on one of the first or second images, and combining the measured length and width with the measurement of the shortest path to compute a volume of feature of interest.

In some implementations the volume is a tumor volume.

In some implementations the measured shortest path is used to compute a trajectory for insertion of a medical device.

In some implementations the method includes expanding at least one of the first and second 2-dimensional images prior to selecting a point of interest.

In some implementations the method further includes co-registering the first 2-dimensional image and the second 2-dimensional image.

In some implementations the method further includes using the converted measurement to calculate a tumor volume.

In some implementations the method further includes using the converted measurement to calculate a needle trajectory.

The present disclosure also provides non-transitory computer-readable media coupled to one or more processors and having instructions stored thereon which, when executed by the one or more processors, cause the one or more processors to perform operations in accordance with implementations of the methods provided herein.

The present disclosure further provides a system for implementing the methods provided herein. The system includes one or more computers and one or more storage devices storing instructions that are operable, when executed by the one or more computers, to cause the one or more computers to perform operations in accordance with implementations of the methods provided herein.

Described herein is a method of accurately measuring 3-dimensional anatomical structures from a sequence of 2-dimensional MRI images. The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE FIGURES

Like reference numbers and designations in the various drawings indicate like elements.

DESCRIPTION

This specification describes a system that can make 3-D measurements of anatomical or medical objects or structures.

Figure 1A:
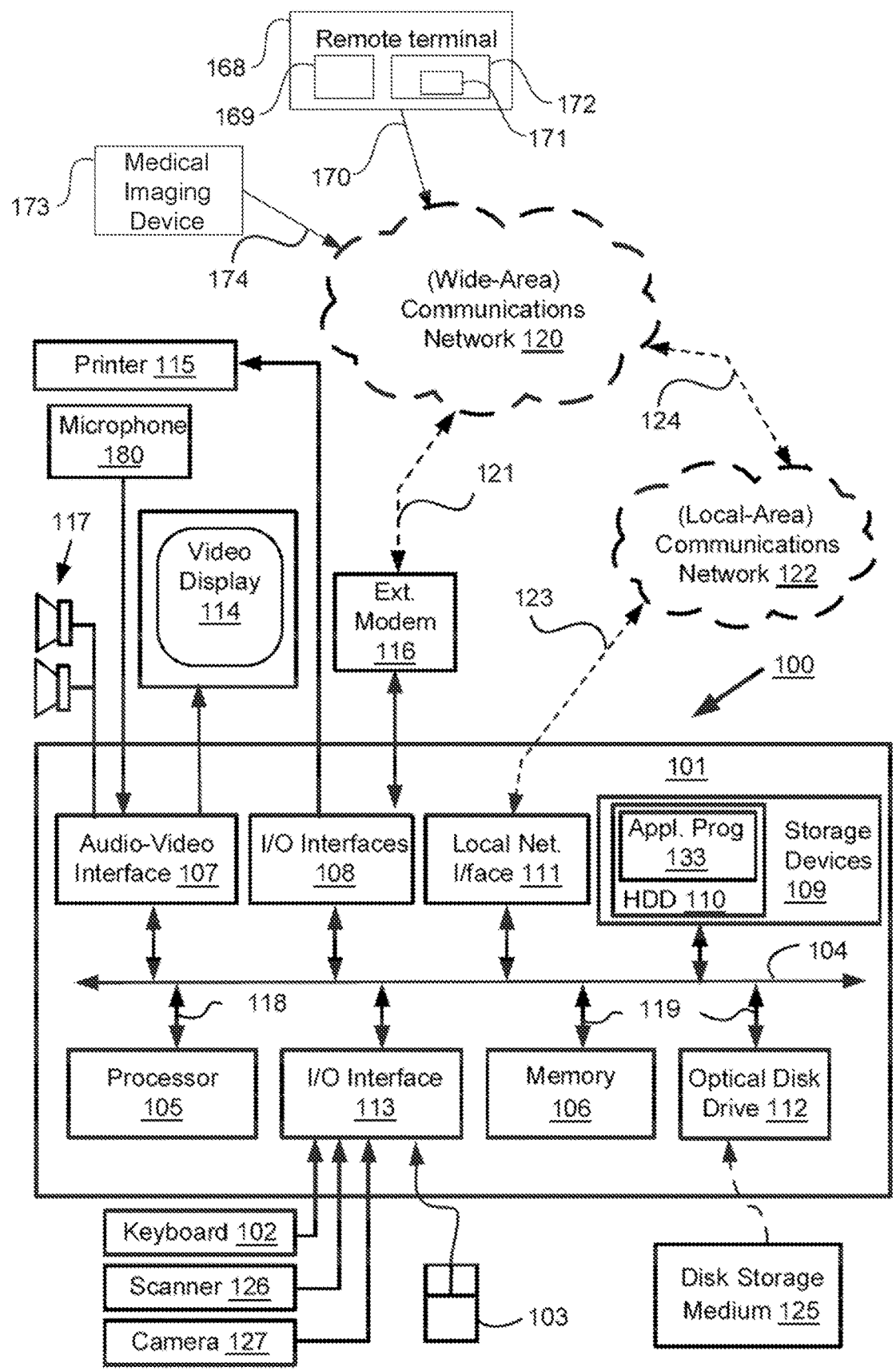
FIG. 1A and FIG. 1B are block diagrams that illustrate an example computer system for use in processing medical images.
Figure 1B:
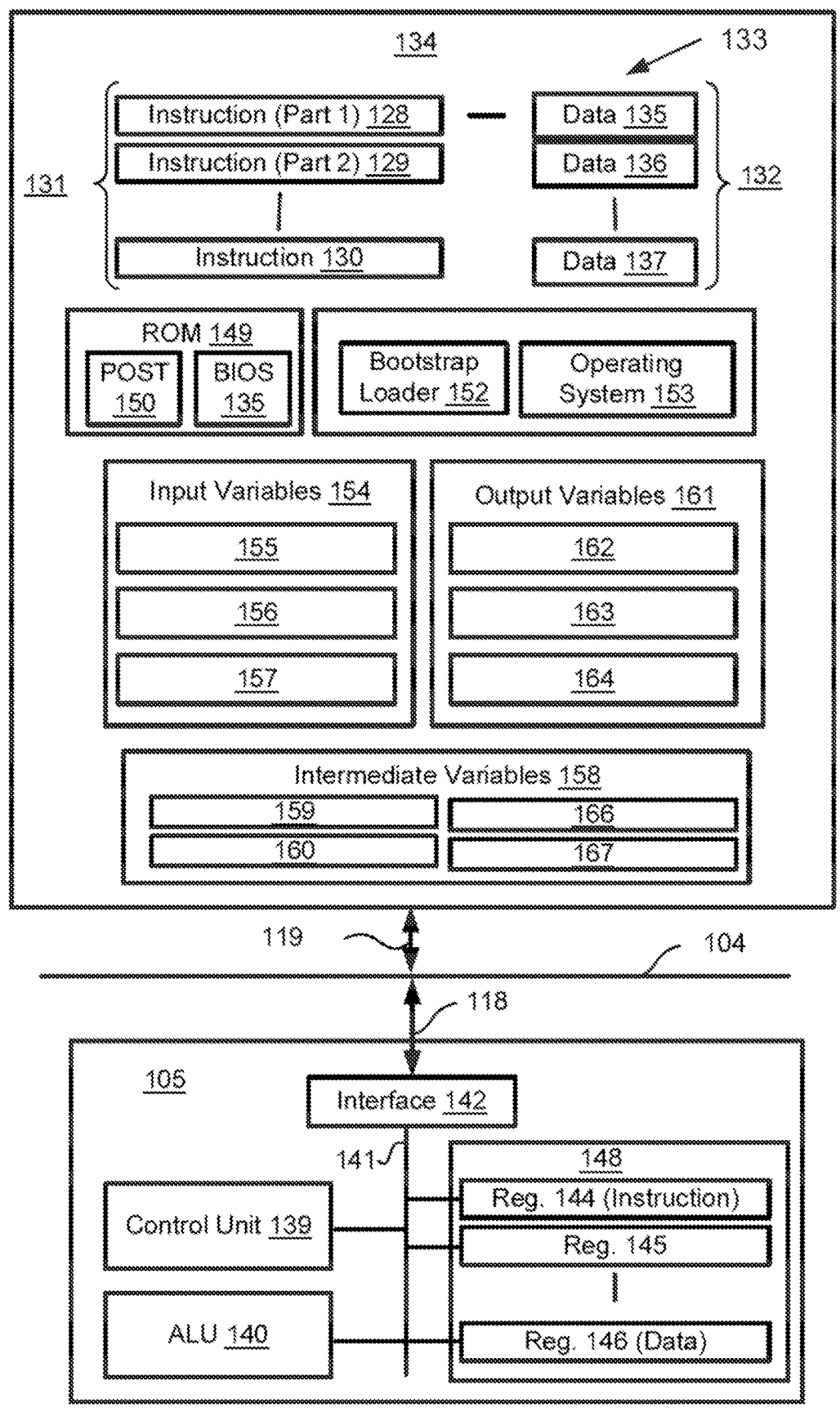

FIGS. 1A and 1B are block diagrams of a computer system 100 upon which one can practice arrangements described in this specification. The following description is directed primarily to a computer server module 101. However, the description applies equally or equivalently to one or more remote terminals 168.

As seen in FIG. 1A, the computer system 100 includes: the server computer module 101; input devices such as a keyboard 102, a pointer device 103 (e.g., a mouse), a scanner 126, a camera 127, and a microphone 180; and output devices including a printer 115, a display device 114 and loudspeakers 117. An external Modulator-Demodulator (Modem) transceiver device 116 may be used by the computer server module 101 for communicating to and from the remote terminal 168 over a computer communications network 120 via a connection 121 and a connection 170. The aforementioned communication can take place between the remote terminal 168 and "the cloud" which in the present description comprises at least the one server module 101. The remote terminal 168 typically has input and output devices (not shown) which are similar to those described in regard to the server module 101. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer server module 101 typically includes at least one processor unit 105, and a memory unit 106. For example, the memory unit 106 may have semiconductor random access memory (RAM) and semiconductor read only memory (ROM). The remote terminal 168 typically includes as least one processor 169 and a memory 172. The computer server module 101 also includes a number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may include an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial or parallel connectivity; the former may be implemented according to the Universal Serial Bus (USB) standards and having corresponding USB connectors (not illustrated). Storage memory devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119.

The techniques described in this specification may be implemented using the computer system 100, e.g., may be implemented as one or more software application programs 133 executable within the computer system 100. In some implementations, the one or more software application programs 133 execute on the computer server module 101 (the remote terminal 168 may also perform processing jointly with the computer server module 101), and a browser 171 executes on the processor 169 in the remote terminal, thereby enabling a user of the remote terminal 168 to access the software application programs 133 executing on the server 101 (which is often referred to as "the cloud") using the browser 171. In particular, the techniques described in this specification may be effected by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules performs the described techniques and a second part and the corresponding code modules manage a user interface between the first part and the user.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product. Software modules for that execute techniques described in this specification may also be distributed using a Web browser.

The software 133 is typically stored in the HDD 110 or the memory 106 (and possibly at least to some extent in the memory 172 of the remote terminal 168). The software is loaded into the computer system 100 from a computer readable medium, and executed by the computer system 100. Thus, for example, the software 133, which can include one or more programs, may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. For example, through manipulation of the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 can execute. The POST program 150 can be stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 can activate the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high-level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source 173, e.g., a medical imaging device 173 such as an MRI or DTI scanner, X-ray, ultrasound or other medical imaging device across one of the networks 120, 122, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

Some techniques described in this specification use input variables 154, e.g., data sets characterizing one or more anatomical or surgical structures, which are stored in the memory 134 in corresponding memory locations 155, 156, 157. The techniques can produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle can include i) a fetch operation, which fetches or reads an instruction 131 from a memory location 128, 129, 130; ii) a decode operation in which the control unit 139 determines which instruction has been fetched; and iii) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the techniques described in this specification may be associated with one or more segments of the program 133 and is performed by the register section 144, 145, 146, the ALU 140, and the control unit 139 in the processor 105 working together to perform the fetch, decode, and execute cycles for every instruction in the instruction set for the noted segments of the program 133. Although a cloud-based platform has been described for practicing the techniques described in this specification, other platform configurations can also be used. Furthermore, other hardware/software configurations and distributions can also be used for practicing the techniques described in this specification.

Figure 2:
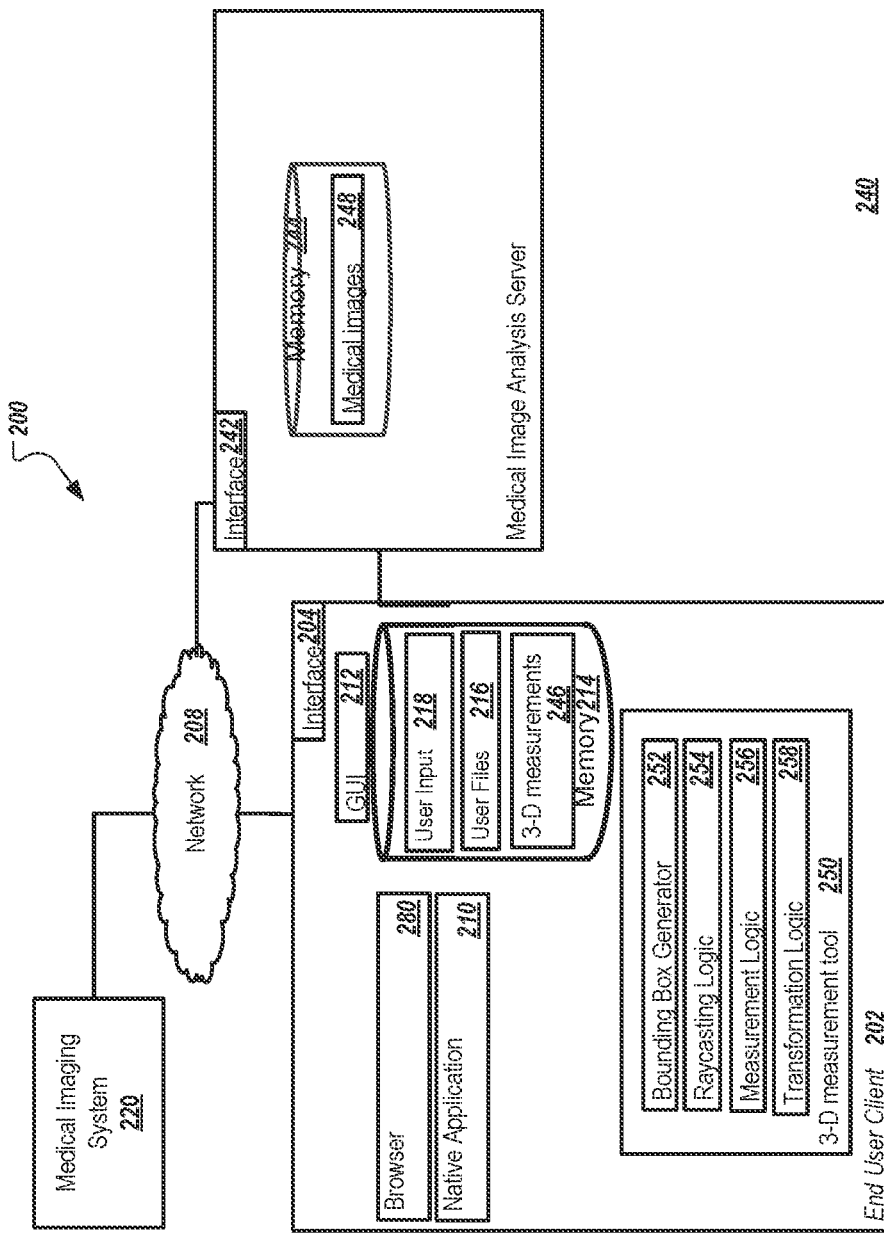
FIG. 2 is a block diagram of an example system for making 3-D measurements of anatomical structures on medical images.

FIG. 2 is a block diagram illustrating an example system for making 3-D measurements of anatomical structures on medical images. The system of FIG. 2 may be implemented within a computer system as described with reference to FIGS. 1A and 1B. Specifically, the illustrated system 200 includes or is communicably coupled with a Medical Image Analysis server 240, an end-user client device 202, a network 208 (which can include a local area network (LAN), a wide area network (WAN), the Internet, or a combination thereof), and a medical imaging system 220. Although shown separately, in some implementations, functionality of two or more systems, devices, or servers may be provided by a single system or server. In some implementations, the functionality of one illustrated system, server, or engine may be provided by multiple systems, servers, or engines, respectively.

An end-user client device 202 (also referred to herein as client device 202 or device 202) is an electronic device that is capable of requesting and receiving content over the network 208. The end-user client device 202 can include any client computing device such as a laptop/notebook computer, wireless data port, smart phone, personal data assistant (PDA), tablet computing device, one or more processors within these devices, or any other suitable processing device that can send and receive data over the network 208. For example, the end-user client device 202 can include, e.g., a computer that includes an input device, such as a keypad, touch screen, or other device that can accept user information, and an output device that conveys information, e.g., associated with the operation of the Medical Image Analysis server 240, or the client device itself, including digital data, visual information, or the GUI 212.

The end-user client device 202 typically includes one or more applications, such as a browser 280 or a native application 210, to facilitate sending and receiving of content over the network 108. Examples of content presented at a client device 202 include images from medical imaging system 220.

Medical imaging system 220 can be any appropriate imaging system, for example an MRI system, CT system, X-ray system, ultrasound system, etc. While only one medical imaging system 220 is shown in FIG. 2 images can be received from one or more medical imaging systems.

Figure 3:
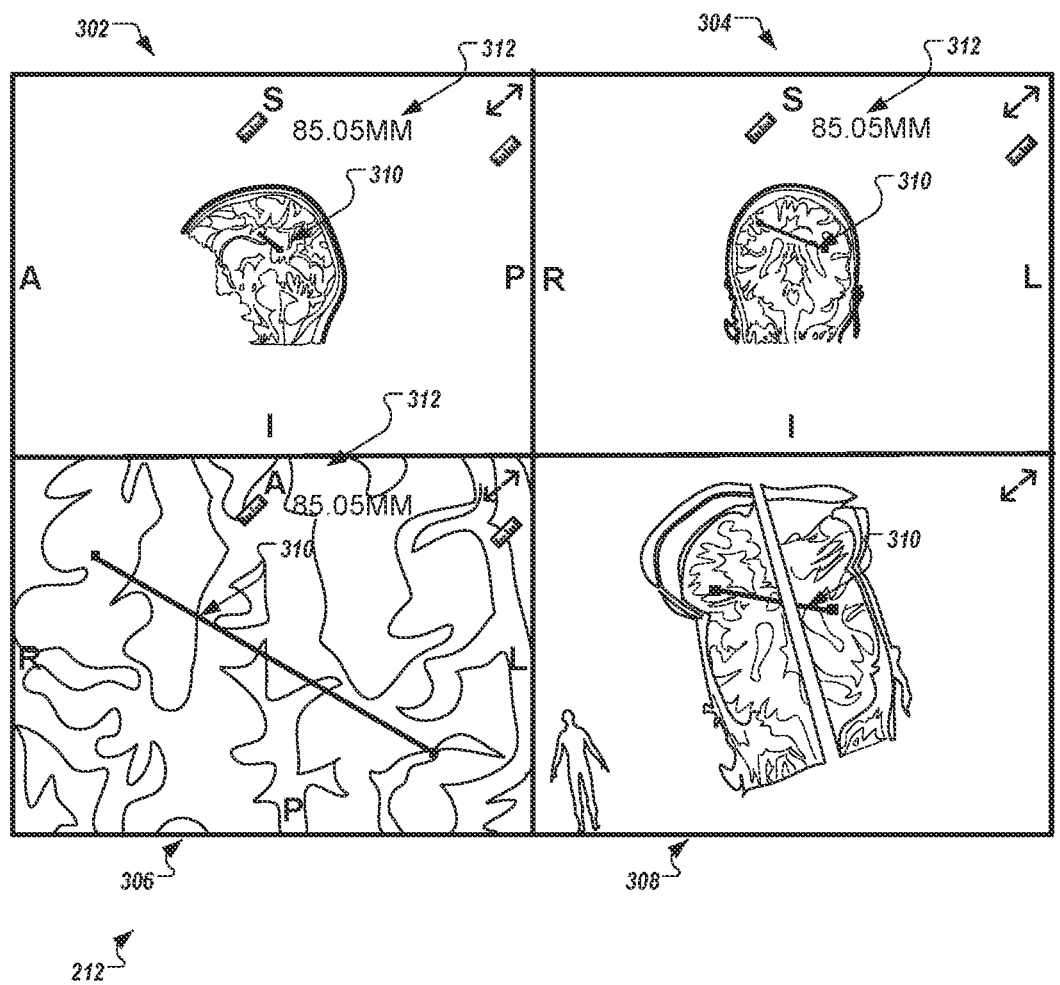
FIG. 3 is a schematic diagram of an example graphical user interface (GUI) representation of making 3-D measurements of anatomical structures.
Figure 4:
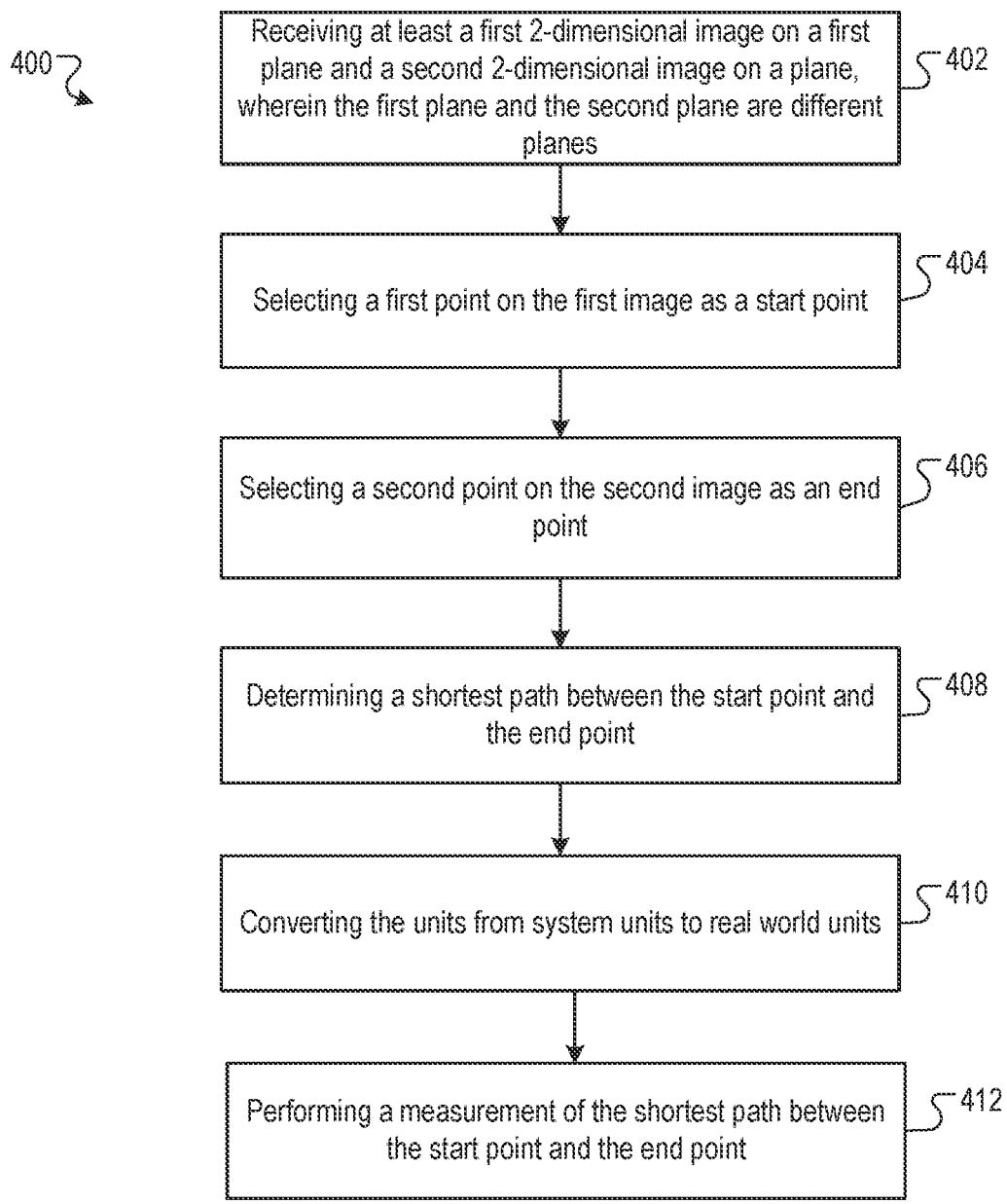
FIG. 4 is a flow diagram of an example method for carrying out 3-D measurement.

As described further with reference to FIGS. 3 and 4, an end user, of the end-user client device 202 may desire to use a 3-D measurement engine 250. In a first implementation 3-D measurement engine 250 can be located at the end-user client device. However, in another implementation the 3-D measurement engine can be located at Medical Image Analysis server 240, or another cloud server to carry out one or more tasks associated with analyzing one or more medical images. For example, a user may analyze medical images of different modalities (e.g., MRI/ultrasound/CT) to obtain different information on one or more anatomical structures, e.g., a human brain. To do that, the end user of the client device 202 can access the Medical Image Analysis server 240. The end user client device 202 provides this interface for display via its graphical user interface (GUI) 212.

On this interface, the end user can provide input 218. The user input can include for example one or more selections on one or more medical images, e.g., an MRI image to make a measurement of an anatomical structure. Once the end user enters and submits this information on the interface, the 3-D measurement engine 250 processes this data to determine a measurement of an anatomical structure 252 based on two or more 2 dimensional images, wherein the 2 or more 2 dimensional images are medical images 248, stored at the Medical Imaging Analysis server 240 and served to the end-user client 202. The two or more 2 dimensional images being on different imaging planes, e.g., sagittal, coronal, axial, oblique, etc. The two or more 2-dimensional images can be on different planes that have a specified spatial relationship to each other, e.g., parallel or orthogonal to one another. For example, if the planes are parallel to each other they may have a specified spacing between them.

3-D measurement engine 250 can include bounding box generation logic 252 used to compute a bounding box around a first and second point on a medical image 248. The first and second point can be selected by a user using a selection tool, e.g., pointer device 103. 3-D measurement engine 250 can further include raycasting logic 254. The cast rays can be used along with measurement logic 256 to compute the shortest path from the first point to the second point. Transformation logic 258 is used to transform the measurement of the shortest path from system co-ordinates to real-world co-ordinates, e.g., millimeters. More details of the method of computing 3-D measurements using 3-D measurement engine 250 are described with reference to FIG. 4.

In some implementations, the end user of the client device 202 can store the received Medical Image Analysis data 218 in the client device 202's memory 214 (along with other user files 216 that may already be stored in the memory 214).

In general, the end-user client device 202 is an electronic computer device operable to receive, transmit, process, and store any appropriate data associated with the system 200 of FIG. 2. The end-user client device 202 can include one or more client applications (as described above). A client application is any type of application that allows the end-user client device 202 to request and view content on a respective client device. In some implementations, a client application can use parameters, metadata, and other information received at launch to access a particular set of data from the Medical Image Analysis server 240. In some instances, a client application may be an agent or client-side version of the one or more enterprise applications running on an enterprise server (not shown).

Memory 214 and memory 244 included in the end-user client device 202, may each include any memory or database module and may take the form of volatile or non-volatile memory including, without limitation, magnetic media, optical media, random access memory (RAM), read-only memory (ROM), removable media, or any other suitable local or remote memory component.

FIG. 3 is a schematic diagram of an example graphical user interface (GUI) representation to facilitate 3-D measurements of anatomical structures, e.g., GUI 212. The GUI can be used for generating and/or displaying a visual representation (or data that provides a visual representation) provided by the Medical Image Analysis server 240. GUI 212 contemplates any suitable graphical user interface, such as a combination of a generic web browser, intelligent engine, and command line interface (CLI) that processes information and efficiently presents the results to the user visually. In an implementation GUI 212 may be used to present the one or more medical images to the end user of the system to facilitate (e.g., by the user specifying a start point and an end point) one or more 3-Dimensional measurements (e.g., of the distance between specified points) or of the volume of an object specified by the user.

In an implementation GUI 212 displays a first image 302. The first image 302 (shown in the top left panel of FIG. 3) can be, in an example, an MRI image in a 2-D plane. In the example shown in FIG. 3, the MRI image is a vertical slice through a human brain. The directions in first image 302 are denoted by the letters S (superior, e.g., above), I (inferior, e.g., below), A (anterior, e.g., in-front), and P (posterior, e.g., behind).

GUI 212 can further display a second image 304 (shown in the top right panel of FIG. 3). The second image 304 can be a MRI image of a different portion of the subject's brain (e.g., either 1) a 2-D image defining a plane parallel to, and spaced a specified distance from, the plane of the first image or 2) a 2-D image defining a plane orthogonal to the plane from the first image). The second image can be a different image format from the first image. The file format can be different. The imaging type can be different (t2 vs t1 vs FLARE vs MPRAGE, etc., MRI vs CAT, etc.). The first image 302 and the second image 304 are co-registered prior to making a 3-D measurement.

In the example shown in FIG. 3 the second image 304 is a further vertical slice. The directions in the second image 304 are denoted by the letters S (superior, e.g., above), I (inferior, e.g., below), R (right), and L (left). That is, the second image 304 is an orthogonal image to the first image.

GUI 212 further displays a third image 306 (shown in the bottom left panel). The second image 306 can be a further MRI image, or can be a different image format. In the example shown in FIG. 3 the MRI image is a further vertical slice through a human brain. The directions in third image 306 are denoted by the letters A (anterior, e.g., in-front), and P (posterior, e.g., behind), R (right), and L (left). That is, the third image 306 is an orthogonal image to the first image and the second image.

GUI 212 can further display a combined image 308 (shown in the bottom right panel), the combined image may be an image constructed from one or more of the 2-D images to enable an end user to view 3-D structures. For example, combined image 308 may be constructed from first image 302, second image 304, and/or third image 306.

In an example a user can click on a first point in a first image and a second point in a second image. Using the techniques described below with reference to FIG. 4 the system can compute a distance in 3 dimensions between the first selected point and second selected point. The computed distance 308 can be shown on each displayed image. The computed distance 310 can further be displayed in real world co-ordinates 312 on one or more of the displayed images. Raycasting can be used to determine the system space coordinates on the planes corresponding to the user clicks. Stated differently, determining the system space coordinates corresponding to the user clicks (in response to the display of the images) is a projection from a 2D space (coordinates in their browser window displaying the images in 2-D planes) into 3D space where the Axial/Sagittal/Coronal/Oblique planes are oriented. Once the 3D system coordinates are determined and transformed to world space via an affine transformation as described, the distance is computed from those points using a standard geometric function like: $d = ((x_2-x_1)_2 + (y_2-y_1)^2 + (z_2-z_1)_2)^{1/2}$.

In an example, the user can click on a 2d image at coordinates (182, 205) (relative to the top left of the 2D image in "screen space"). Raycasting is used to determine the 3D system coordinate: (37.55740609803376, −6.876112612399137, −11.959092140197754). These are world space coordinates (mm) as the following affine transform has already been applied to the image in order to visualize it correctly:

[0.4687998294830322, 0, 0, −125.13728332519531
0, 0.4687998294830322, 0, −135.87200927734375
0, 0, 0.4687998294830322, −160.09983825683594
0, 0, 0, 1]

The affine transform is a 4×4 matrix, shown here in row-major order.

Computed distance 310 may be used for one or more medical techniques. For example, measurements in 3 planes of a tumor can be used to calculate highly accurate radiation doses. In another example, measurements in 3 planes may be used to calculate the trajectory of a needle or other surgical instrument for use in a surgical procedure, e.g., spinal injections or other surgical procedures.

FIG. 4 is a diagram of an example method for carrying out 3-D measurement. The method may be implemented using a user interface, such as the user interface described herein in more detail with reference to FIGS. 2-3.

The method includes the receiving 402 at least a first 2-dimensional image on a first plane and a second 2-dimensional image on a second plane, wherein the first plane and the second plane are different planes. The images can include any data characterizing one or more aspects of an anatomical structure, for example, a tumor, blood vessel, human organ, etc. Each 2-dimensional image may be an image taken on the axial, sagittal, or coronal plane. The images can be from the same set of imaging data (e.g., MRI data, X ray data, and/or ultrasound data) of an anatomical structure. The plane of the first 2-dimensional image can have different relative orientations to the plane of the second 2-dimensional image. For example, the planes of the images can be parallel to each other or they can be orthogonal to one another.

In an example, the first image is selected from a sequence of 2-dimensional medical images on the first plane, the sequence of images being images of a human organ, and the start point is a first point of interest The sequence can be a sequence of 2-dimensional images which are each parallel in an x-y plane but spaced along a z-dimension. The user can scan through the images to select a starting point for making a measurement. Similarly, the second image can be selected from a sequence of 2-dimensional medical images on a second plane, the sequence of images being images of a human organ, and the end point is a second point of interest in the second image.

Using an input device, e.g., pointer device 103, a user can select 404 on a user interface (e.g., the user interface described in more detail with reference to FIG. 3) a first point on the first image as a start point. The user can further select 406 on a user interface a second point on the second image as an end point.

The shortest path between the start point and the end point can be determined 408 by performing raycasting to determine the shortest path between the start point and the end point. Converting 410 the measurement from system units to real world units, can include, in an implementation executing an affine transformation, i.e., a transformation that preserves lines and distances. The affine transformation can be calculated as described above.

The shortest path between the start point and the end point can be measured 412 using a geometric function. Given the dimensions of the first image and the second image are known, it's possible to measure the distance from those points using a standard geometric function, e.g., $$d = ((x2-x1)^2 + (y2-y1)^2 + (z2-z1)^2)^{\frac{1}{2}}.$$

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal which is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network.

Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products. Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method of measuring 3-dimensional distances on medical images of a human brain comprising;
    receiving at least a first 2-dimensional image, of a first slice of a human brain, on a first plane and a second 2-dimensional image, of a second slice of the human brain, on a second plane, wherein the first plane and the second plane are different planes and wherein at least one of the first 2-dimensional image and the second 2-dimensional image is selected from a sequence of 2-dimensional images of the human brain where the images are each parallel in an x-y plane but spaced along a z-direction;
    receiving user input selecting a first point on the first 2-dimensional image as a start point;
    receiving user input selecting a second point on the second 2-dimensional image as an end point;
    determining a shortest 3-dimensional path between the start point on the first 2-dimensional image in the first plane and the end point on the second 2 dimensional image in the second plane;
    performing a measurement of the shortest path between the start point and the end point; and,
    calculating a brain tumor volume based at least in part on the measurement.

2. The method of claim 1 wherein determining a shortest path between the start point and the end point comprises:
    performing raycasting to determine a projection of the co-ordinates of the first selected point on the first 2-dimensional image and the second selected point on the second selected image from 2-dimensional space to three dimensional space.

3. The method of claim 1 wherein performing the measurement comprises converting the projected co-ordinates from system units to real world units including performing an affine transformation; and measuring the distance between the first selected point and the second selected point using a geometric function.

4. The method of claim 1 wherein the first plane and the second plane are each selected from axial, sagittal, coronal, and oblique planes.

5. The method of claim 1 wherein;
    the first image is selected from a sequence of 2-dimensional medical images on the first plane, the sequence of images being images of a human brain, and the start point is a first point of interest; and,
    the second image is selected from a sequence of 2-dimensional medical images on the second plane, the sequence of images being images of a human brain, and the end point is a second point of interest.

6. The method of claim 1 wherein the first image and the second image are orthogonal to each other.

7. The method of claim 1 further comprising:
    measuring a length and a width of a feature on one of the first or second images; and
    combining the measured length and width with the measurement of the shortest path to compute a volume of a feature of interest and to calculate a radiation dose.

8. The method of claim 7 wherein the volume is a tumor volume.

9. The method of claim 1 further comprising expanding at least one of the first and second 2-dimensional images prior to selecting a point of interest.

10. The method of claim 1 further comprising co-registering the first 2-dimensional image and the second 2-dimensional image.

11. The method of claim 1 wherein the action further comprises using the measurement to calculate a needle trajectory.

12. A system comprising one or more computers and one or more storage devices storing instructions that are operable, when executed by the one or more computers, to cause the one or more computers to perform operations comprising:
    receiving at least a first 2-dimensional image, of a first slice of a human brain, on a first plane and a second 2-dimensional image, of a second slice of the human brain, on a second plane, wherein the first plane and the second plane are different planes and wherein at least one of the first 2-dimensional image and the second 2-dimensional image is selected from a sequence of 2-dimensional images of the human brain where the images are each parallel in an x-y plane but spaced along a z-direction;

receiving user input selecting a first point on the first image as a start point;

receiving user input selecting a second point on the second image as an end point;

determining a shortest 3-dimensional path between the start point on the first 2-dimensional image in the first plane and the end point on the second 2-dimensional image in the second plane;

performing a measurement of the shortest path between the start point and the end point; and, taking an action based on the measurement.

13. One or more non-transitory storage media storing instructions that when executed by one or more computers cause the one or more computers to perform operations comprising:

receiving at least a first 2-dimensional image, of a first slice of a human brain, on a first plane and a second 2-dimensional image, of a second slice of the human brain, on a second plane, wherein the first plane and the second plane are different planes and wherein at least one of the first 2-dimensional image and the second 2-dimensional image is selected from a sequence of 2-dimensional images of the human brain where the images are each parallel in an x-y plane but spaced along a z-direction;

receiving user input selecting a first point on the first image as a start point;

receiving user input selecting a second point on the second image as an end point;

determining a shortest 3-dimensional path between the start point on the first 2-dimensional image in the first plane and the end point on the second 2-dimensional image in the second plane;

performing a measurement of the shortest path between the start point and the end point; and, calculating a brain tumor volume based at least in part on the measurement.

14. The one or more non-transitory storage media storing instructions of claim 13 wherein determining a shortest path between the start point and the end point comprises:

performing raycasting to determine a projection of the co-ordinates of the first selected point on the first 2-dimensional image and the second selected point on the second selected image from 2-dimensional space to three dimensional space.

15. The one or more non-transitory storage media storing instructions of claim 13 wherein taking an action comprises converting the projected co-ordinates from system units to real world units including performing an affine transformation; and measuring the distance between the first selected point and the second selected point using a geometric function.

16. The one or more non-transitory storage media storing instructions of claim 13 wherein the first plane and the second plane are each selected from axial, sagittal, coronal, and oblique planes.

17. The one or more non-transitory storage media storing instructions of claim 13 wherein;

the first image is selected from a sequence of 2-dimensional medical images on the first plane, the sequence of images being images of a human brain, and the start point is a first point of interest; and, the second image is selected from a sequence of 2-dimensional medical images on the second plane, the sequence of images being images of a human brain, and the start end point is a second point of interest.

18. The one or more non-transitory storage media storing instructions of claim 13 wherein the first image and the second image are orthogonal to each other.

19. A method of measuring 3-dimensional distances on medical images comprising;

receiving at least a first 2-dimensional image, of a first slice of a human brain, on a first plane and a second 2-dimensional image, of a second slice of the human brain, on a second plane, wherein the first plane and the second plane are different planes and wherein at least one of the first 2-dimensional image and the second 2-dimensional image is selected from a sequence of 2-dimensional images of the human brain where the images are each parallel in an x-y plane but spaced along a z-direction;

receiving user input selecting a first point on the first 2-dimensional image as a start point;

receiving user input selecting a second point on the second 2-dimensional image as an end point;

determining a shortest 3-dimensional path between the start point on the first 2-dimensional image in the first plane and the end point on the second 2 dimensional image in the second plane;

performing a measurement of the shortest path between the start point and the end point; and, computing a trajectory for insertion of a medical device based at least in part on the measurement.

* * * * *